United States Patent
Hill et al.

(10) Patent No.: US 8,655,459 B2
(45) Date of Patent: Feb. 18, 2014

(54) MEDICAL IMPLANTABLE LEAD AND METHOD FOR MOUNTING THE SAME

(75) Inventors: Rolf Hill, Järfälla (SE); Olof Stegfeldt, Älta (SE)

(73) Assignee: St. Jude Medical AB (SE)

( * ) Notice: Subject to any disclaimer, the term of this patent is extended or adjusted under 35 U.S.C. 154(b) by 1111 days.

(21) Appl. No.: 12/602,535

(22) PCT Filed: Jun. 13, 2007

(86) PCT No.: PCT/SE2007/000582
§ 371 (c)(1),
(2), (4) Date: Dec. 1, 2009

(87) PCT Pub. No.: WO2008/153451
PCT Pub. Date: Dec. 18, 2008

(65) Prior Publication Data
US 2010/0217107 A1 Aug. 26, 2010

(51) Int. Cl.
*A61N 1/05* (2006.01)
(52) U.S. Cl.
USPC .......................................... 607/127; 607/122
(58) Field of Classification Search
USPC ................................................ 607/127, 122
See application file for complete search history.

(56) References Cited

U.S. PATENT DOCUMENTS

| | | | |
|---|---|---|---|
| 4,217,913 A * | 8/1980 | Dutcher | 607/127 |
| 4,886,074 A | 12/1989 | Bisping | |
| 5,716,390 A | 2/1998 | Li | |
| 5,837,006 A | 11/1998 | Ocel et al. | |
| 5,948,015 A | 9/1999 | Hess et al. | |
| 2002/0188340 A1 | 12/2002 | Bischoff et al. | |
| 2002/0193860 A1 | 12/2002 | Bischoff et al. | |
| 2003/0040787 A1* | 2/2003 | Flynn et al. | 607/122 |
| 2003/0144722 A1 | 7/2003 | Soltis et al. | |
| 2007/0129782 A1 | 6/2007 | Feldmann et al. | |
| 2008/0004682 A1 | 1/2008 | Wengreen et al. | |

* cited by examiner

*Primary Examiner* — Christopher D Koharski
*Assistant Examiner* — Michael Carey

(57) ABSTRACT

In a medical implantable lead and method for monitoring and/or controlling of an organ inside a human or animal body, the lead has a helix in a distal end that is rotatable by an inner wire coil (5), which is disposed inside of and along essentially the entire length of the lead and which is rotatably arranged in relation to an outer sleeve, such that the helix is attachable to the organ by being screwed into the tissue inside the body. The lead is provided with a connector in a proximal end which is connectible to an electronic device for monitoring or controlling the function of the organ, the connector having a connector pin that is in engagement with the wire coil and that is rotatably journaled inside a connector housing. During mounting of the medical implantable lead to the organ, the inner wire coil is rotatable by rotating the connector pin in relation to the connector housing with a suitable tool. The connector is provided with a friction brake between the connector pin and the connector housing.

8 Claims, 3 Drawing Sheets

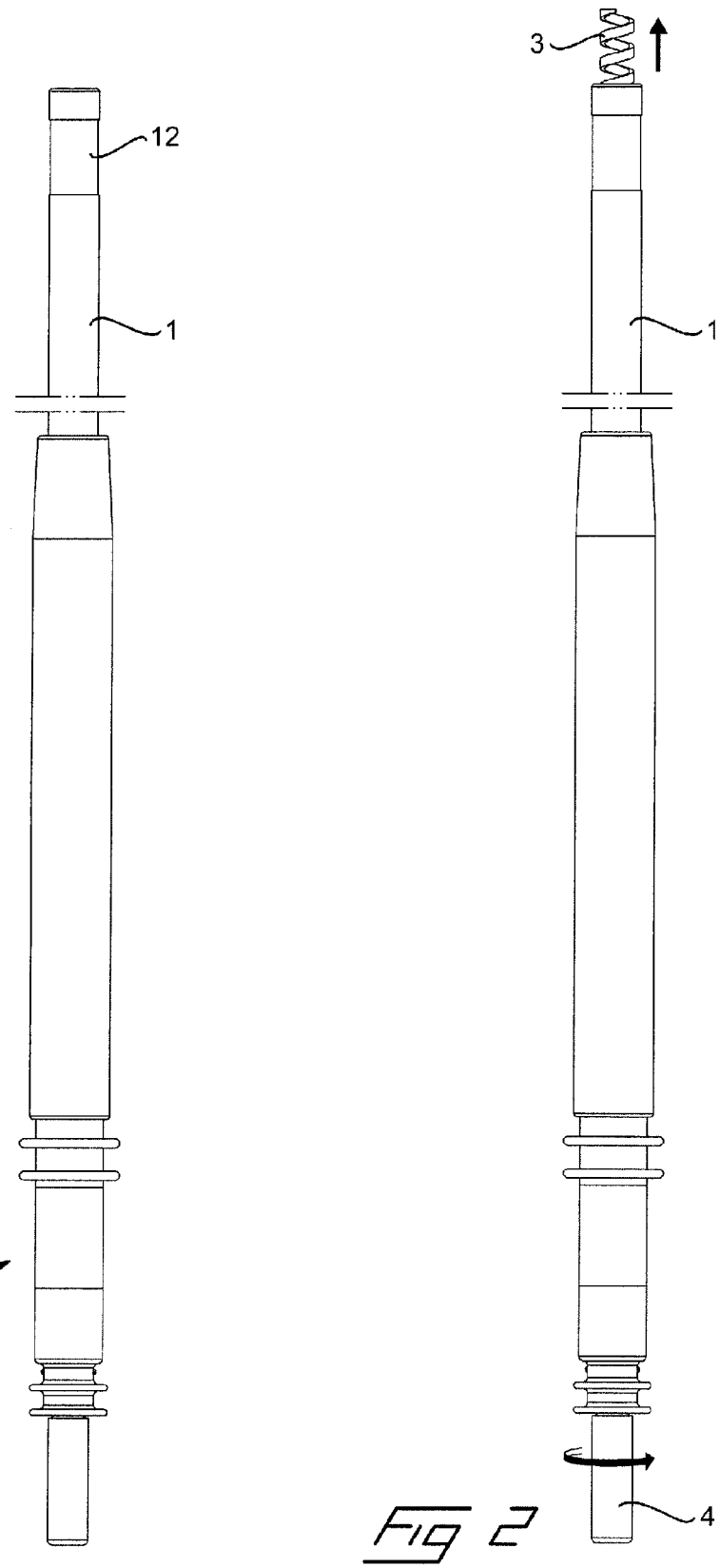

MEDICAL IMPLANTABLE LEAD AND METHOD FOR MOUNTING THE SAME

BACKGROUND OF THE INVENTION

1. Field of the Invention

The present invention relates to a medical implantable lead for monitoring and/or controlling of an organ inside a human or animal body, the lead being of the type having a helix in a distal end which is rotatable by means of an inner wire coil, which is disposed inside of and along essentially the hole length of the lead and which is rotatably arranged in relation to an outer sleeve, such that the helix is attachable to the organ by being screwed into the tissue inside the body, wherein the lead is provided with a connector in a proximal end which is connectible to an electronic device for monitoring or controlling the function of the organ, the connector having a connector pin that is in engagement with the wire coil and that is rotatably journaled inside a connector housing such that, during mounting of the medical implantable lead to the organ, the inner wire coil is rotatable by rotating the connector pin in relation to the connector housing by means of a suitable tool.

The invention also relates to a method for mounting a medical implantable lead to an organ inside a human or animal body.

2. Description of the Prior Art

Medical implantable leads for monitoring and/or controlling of an organ inside a human or animal body, are well known in the art, e.g. medical implantable leads for monitoring and controlling the activity of a human heart, which are adapted to be attached to the heart in the distal end and is connected to a pacemaker or an implantable cardiac defibrillator in its proximal end. A common type of such leads is attached to the organ by means of a helix, which is screwed out from the distal end and into the tissue. One way to perform the rotation of the helix is by means of a rotatable inner wire coil, which is located inside and extended along the whole length of the lead. The inner coil is connected to the helix in its distal end and to a connector pin at a connector in its proximal end which projects from the distal end and is rotatably journaled in a connector housing. The connector is adapted to subsequently be connected electrically to the electronic equipment, wherein the inner coil is utilized as an electrical conductor with the connector pin electrically connected to the equipment and the helix as an electrode inside the tissue. However, during mounting of the lead, the projecting connector pin and the inner coil is used to rotate the helix, by means of a suitably tool, to thereby accomplish screwing in of the helix into the tissue and attachment of the lead.

However, the inner coil has a considerable inherent resilience, which has to result that the physician performing the rotating of the inner coil can not sense when the helix is completely screwed out from the lead. Therefore it is common practice to count the number of turns the connector pin is rotated until it is predetermined to be completely screwed out, and subsequently add a few additional turns of rotation to be sure that the helix really is completely screwed out. This has the effect that a tension will be built up in the inner coil from the moment when the helix is completely screwed out until the rotating is terminated after the additional few turns of rotation. When accordingly the physician releases the tool from the connector pin, it often happens that the inner coil spins back and the speed and the mass inertia of the rotational movement of the inner coil may result in that the helix is wholly or partly screwed out and released from the tissue again. Naturally, if this happens it has to be rectified which will increase implantation time and cause frustration to the physician.

SUMMARY OF THE INVENTION

It is an object of the invention to overcome the disadvantages with prior art leads and provide a medical implantable lead by which the disadvantages with possible back spin during mounting of medical implantable leads of the aforementioned kind are eliminated.

The invention also relates to a method for mounting a medical implantable lead having substantially the same object as above.

The basis of the invention is the insight that the above object may be achieved by providing the connector with a friction brake acting between the connector pin and the connector housing such that the rotary speed between them is reduced.

Within this general idea the invention can be implemented in many different ways. The magnitude of the frictional braking effect between the connector pin and the connector housing, need not be large. It is sufficient that the inner coil is prevented from spinning freely in relation to the connector housing when the rotary actuating tool is removed from the connector pin, such that the inner coil is allowed to slowly rotate back to its relaxed state in a controlled manner. The friction brake prevents the inner coil, due to high rotary speed and mass inertia, from rotating back beyond its relaxed state to a negative tension state which may cause screwing out and releasing of the helix from the tissue. A sufficiently low frictional braking effect will ensure that the operation of screwing out the helix from the distal end of the lead and into the tissue, is not affected negatively.

The friction brake between the connector pin and the connector housing can be realized in many different ways. In the hereinafter given detailed description are described two different embodiments of the friction brake. On the one hand is described one embodiment where the friction brake is achieved by means of an elastic tongue provided in the connector housing, which bears against the outer surface of the connector pin and accordingly causes friction there between when rotating them in relation to each other. Here is also described an embodiment where the friction brake has the form of a ring being slightly deformed in relation to a strictly circular form and being positioned between the connector pin and the connector housing.

However, it is to be understood that also other embodiments of the friction brake are conceivable within the scope of the claims. For example friction brakes between the connector pin and connector housing comprising rings having different forms, such as a C-form or a D-form, or a ball seal, i.e. a ring formed helical spring. Though it is not preferred, it would even be conceivable to provide a friction brake that is not positioned in the boundary between the connector pin and the connector housing, e.g. an elastic tongue, a disc or cantilever member attached to one of the connector pin or connector housing and bearing with its other end against an outer envelope surface or end surface of the other of the connector pin or the connector housing. Moreover, it is conceivable to arrange a friction brake which is non-mechanical, e.g. a viscously operating brake, wherein the connector pin is rotatable within a viscous fluid, a gel or the like, which counteracts the rotational movement of the connector pin by a viscous resistance.

BRIEF DESCRIPTION OF THE DRAWINGS

FIG. 1 is a view from the outside of a medical implantable lead according to the invention.

FIG. 2 is a view according to FIG. 1 with a helix screwed out from a distal end.

DESCRIPTION OF THE PREFERRED EMBODIMENTS

Reference is first made to FIGS. 1 and 2 of the drawings, in which are illustrated a proximal and distal end of a shortened medical implantable lead according to the invention. The depicted lead is adapted for monitoring and controlling the function of a heart and comprises a so called header sleeve 1 in a distal end and a connector 2 for mechanical and electrical connection to an electronic device in form of a pacemaker or an implantable cardiac defibrillator in a proximal end. The lead is adapted to be inserted into a human or animal body in the state depicted in FIG. 1, preferably through a vein. By means of a locator or guiding wire (not shown), which can be inserted through a bore inside the lead from the proximal to the distal end, the lead can be guided to a suitable position inside the heart.

Figures 3, 4:
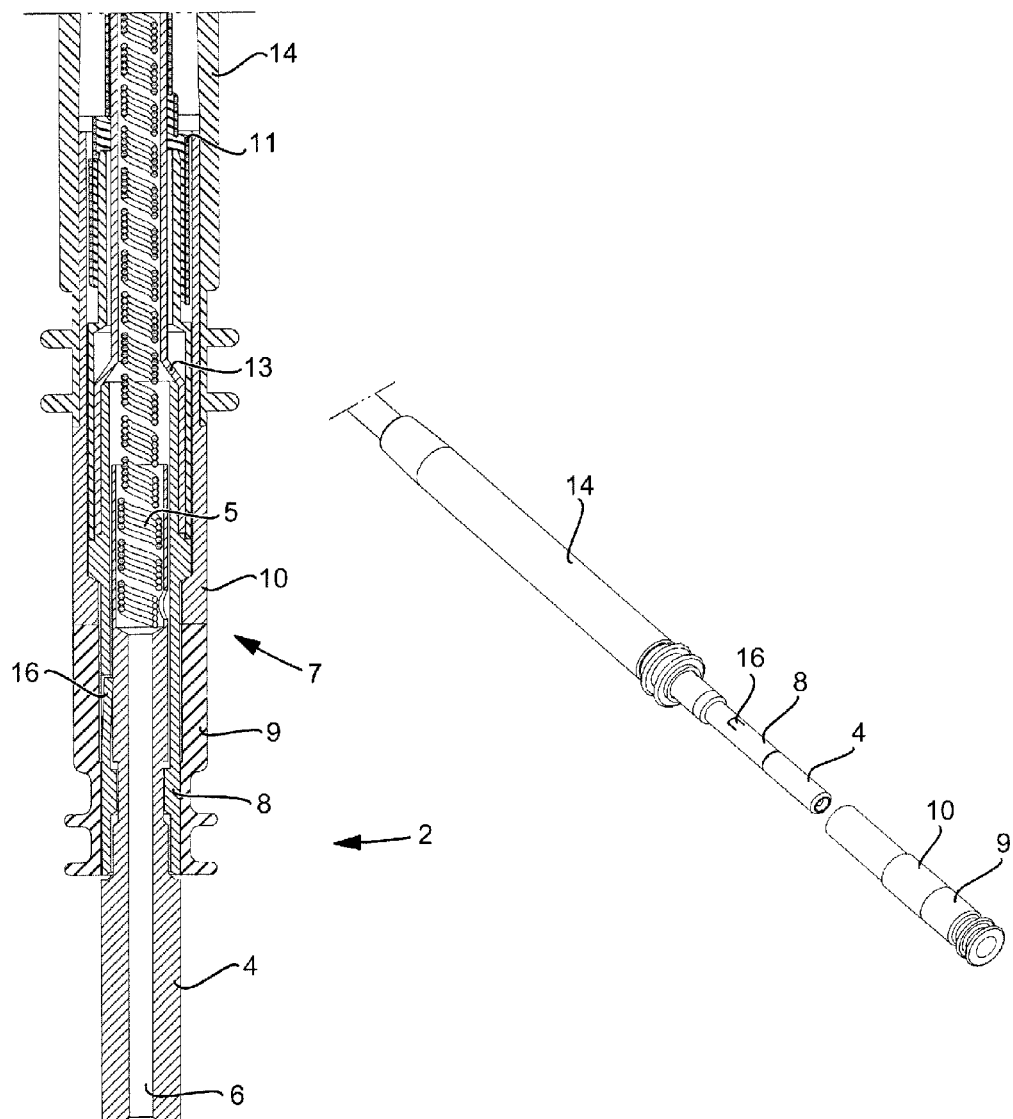
FIG. 3 is an enlarged longitudinal section through a connector in a proximal end of the lead according to a first embodiment.
FIG. 4 is a perspective view of a connector with a connector ring and an outer sealing member removed for exposure of the brake tongue according to the embodiment in FIG. 3.
Figure 5:
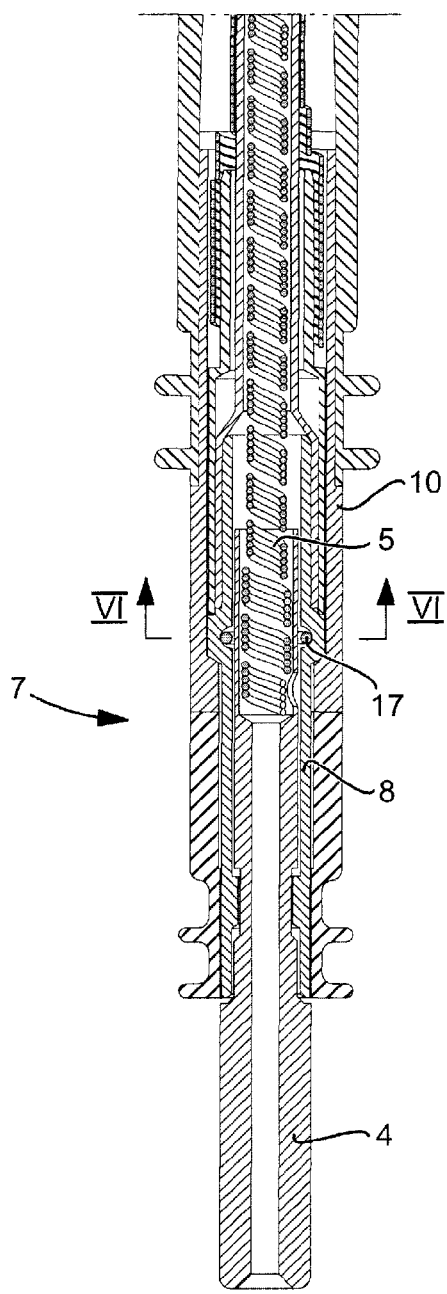
FIG. 5 is a section like FIG. 3 of a second embodiment.

When accordingly the lead is positioned in a suitable position with its distal end surface abutting a heart wall, a helix 3 can be screwed out from inside the header sleeve 1, as is illustrated in FIG. 2, by rotating a connector pin 4 which projects from the proximal end of the lead. As is illustrated in FIGS. 3 and 5, the connector pin 4 is connected to an inner wire coil 5, which is rotatably arranged inside the lead and extends to the distal end of the lead where it is in connection with the helix 3. The rotation of the connector pin 4 can be performed by means of a tool (not shown), such as a clip or the like. Accordingly, when the connector pin 4 is rotated, the rotational motion is transferred via the inner coil 5 to the helix, which thereby can be screwed out of or into the header sleeve 1 as desired. Inside the connector pin 4 and the inner coil 5, an inner bore 6 is defined, through which a guide wire may be inserted during implanting of the lead for guiding the lead to a desired location.

In FIG. 3 is shown a first embodiment of an enlarged longitudinal section through the connector 2. The lead comprises at least two electrical conductor paths of which the connector pin 4 constitutes part of a first of the electrical conductor paths, together with the inner wire coil 5 and the helix 3, which functions as an electrode inside the tissue. The connector pin 4 is accordingly adapted to be connected to a first electrical terminal in the pacemaker or defibrillator. The connector pin 4 is rotatably journaled inside a connector housing 7, which is composed of several different parts. More precisely, the connector housing comprises an inner bearing sleeve 8 of an electrical insulating material, e.g. of a polymer, an outer sealing member 9 of a soft, resilient material, e.g. of silicone, and an outer connector ring 10 of an electrical conductive material, e.g. of metal. The connector ring 10 constitutes part of the second electrical conductor path and accordingly is adapted to be connected to a second electrical terminal in the pacemaker or defibrillator. Besides the connector ring 10, the second electrical conductor path comprises an outer wire coil 11, which is electrical connected to the connector ring 10 and extends to a ring electrode 12 at the distal end.

Naturally, the electrical conductor paths have to be electrical insulated from each other the whole way to the electrodes, i.e. the helix 3 and the ring electrode 12, respectively. The bearing sleeve 8 provides for the electrical insulation between the connector pin 4 and the connector ring 10, whereas an inner tubing 13 of e.g. silicone is positioned between the inner and outer wire coils.

The connector pin 4 and connector housing 7 is held by a connector boot 14 of an electrical insulating material, and an outer tubing surrounds and protects the lead and is attached to the connector boot.

To restrict the rotational speed of the connector pin 4 in relation to the connector housing 7, a friction brake is provided between them. The friction brake is in this embodiment formed as an elastic tongue 16, as is best seen from the perspective view of FIG. 4. The elastic tongue 16 is arranged in the electrical insulating material of the bearing sleeve 8 and bears against the outer surface of the connector pin 4 and accordingly restricts the rotational speed between them.

Figure 6:
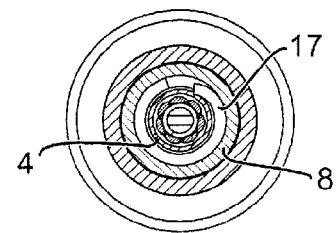
FIG. 6 is a cross section of the brake ring according to the embodiment in FIG. 5.

Now reference is made to FIG. 5 in which is shown a longitudinal section through a connector provided with a friction brake according to a second embodiment of the invention. The lead and the overall structure of the connector are substantially identical with the lead described in relation to FIG. 3, so those parts will not be described once more. However, instead of an elastic tongue, the friction brake in this embodiment is accomplished by means of a ring 17. As is best seen from the cross section of FIG. 6, the ring is accommodated in a groove in the bearing sleeve 8. Moreover the ring 17 is cut and slightly deformed in the vicinity of its cut ends, such that the cut ends will bear against the outer surface of the connector pin 4. The ring will accordingly restrict the rotational speed between the connector pin 4 and the bearing sleeve 8 and accordingly the connector housing 5.

Although modifications and changes may be suggested by those skilled in the art, it is the intention of the inventors to embody within the patent warranted heron all changes and modifications as reasonably and properly come within the scope of their contribution to the art.

We claim:

1. Method for mounting a medical implantable lead to an organ inside a human or animal body for monitoring and/or controlling the organ, comprising:

providing a medical implantable lead comprising a helix in a distal end, an inner wire coil disposed inside of and along essentially the entire length of the lead and which is rotatably arranged in relation to an outer sleeve, a connector in a proximal end which is connectible to an electronic device for monitoring and/or controlling the activity in the organ, the connector comprising a connector pin, which is in engagement with the inner wire coil and which is rotatably journaled inside a connector housing;

inserting the medical implantable lead into the body such that a distal end abuts the organ to be monitored and/or controlled;

attaching the lead to the organ by screwing the helix into the tissue of the organ; and relieving possible built up potential energy in the inner coil, due to over torque of the same during screwing in of the helix, by applying a braking effect by means of a friction brake directly contacting the connector pin.

2. Method according to claim 1, comprising the further step of braking by means of a flexible tongue.

3. Method according to claim 1, comprising the further step of braking by means of a ring.

4. A medical implantable lead for monitoring and/or controlling an organ inside a living subject, said medical implantable lead comprising:
- a lead body having a proximal end and a distal end with an outer sleeve therebetween;
- a helix rotatably mounted at said distal end of said lead body;
- an inner wire coil proceeding through an interior of said outer sleeve substantially between said proximal end and said distal end, and being connected to said helix to rotate said helix when said inner wire coil is rotated;
- a connector at said proximal end of said lead body configured for mechanical and electrical connection to an electronic device for monitoring or controlling functioning of an organ in the living subject, said connector comprising a connector housing and a connector pin rotatably journaled inside said connector housing and engaging said inner wire coil, said inner wire coil being rotated in a first rotational direction by rotating said connector pin relative to said connector housing to, in turn, rotate said helix to affix said helix to tissue of said organ; and
- a friction brake that interacts between said connector pin and said connector housing to prevent rotation of said inner wire coil in a second rotational direction opposite to said first rotational direction.

5. A medical implantable lead as claimed in claim 4 wherein said connector housing comprises a bearing sleeve in which said connector pin is rotatably journaled, and wherein said friction brake is located between said connector pin and said bearing sleeve.

6. A medical implantable lead as claimed in claim 5 wherein said friction brake comprises an elastic tongue in said bearing sleeve that bears against an exterior surface of said connector pin.

7. A medical implantable lead as claimed in claim 5 wherein said friction brake comprises a ring received in said bearing sleeve, said ring bearing against an exterior surface of said connector pin.

8. A medical implantable lead as claimed in claim 4 wherein said friction brake is a viscous brake.

\* \* \* \* \*